United States Patent
Ribani et al.

(10) Patent No.: US 11,951,076 B2
(45) Date of Patent: Apr. 9, 2024

(54) MACHINE AND METHOD FOR FILLING CAPSULES

(71) Applicant: I.M.A. INDUSTRIA MACCHINE AUTOMATICHE S.P.A., Ozzano Dell'emilia (IT)

(72) Inventors: Massimo Ribani, Ozzano Dell'emilia (IT); Maurizio Bedetti, Ozzano Dell'emilia (IT); Alessandro Masotti, Ozzano Dell'emilia (IT)

(73) Assignee: I.M.A. INDUSTRIA MACCHINE AUTOMATICHE S.P.A., Ozzano Dell'Emilia (IT)

(*) Notice: Subject to any disclaimer, the term of this patent is extended or adjusted under 35 U.S.C. 154(b) by 289 days.

(21) Appl. No.: 17/625,150

(22) PCT Filed: Jul. 21, 2020

(86) PCT No.: PCT/IB2020/056819
§ 371 (c)(1),
(2) Date: Jan. 6, 2022

(87) PCT Pub. No.: WO2021/014340
PCT Pub. Date: Jan. 28, 2021

(65) Prior Publication Data
US 2022/0265517 A1    Aug. 25, 2022

(30) Foreign Application Priority Data
Jul. 22, 2019 (IT) .................. 102019000012504

(51) Int. Cl.
*A61J 3/00* (2006.01)
*A23P 10/30* (2016.01)
(Continued)

(52) U.S. Cl.
CPC ............ *A61J 3/074* (2013.01); *A23P 10/30* (2016.08); *A61J 3/10* (2013.01); *A61K 9/4833* (2013.01); *B65B 1/26* (2013.01); *B65B 63/02* (2013.01)

(58) Field of Classification Search
CPC ..................................... A61J 3/074
See application file for complete search history.

(56) References Cited

U.S. PATENT DOCUMENTS

| 4,542,835 A | 9/1985 | Gamberini |
| 6,837,280 B2 | 1/2005 | Ragazzini et al. |
(Continued)

FOREIGN PATENT DOCUMENTS

| CN | 1551753 | 12/2004 |
| CN | 101884596 | 11/2010 |
(Continued)

OTHER PUBLICATIONS

International Search Report dated Nov. 13, 2020 in International (PCT) Application No. PCT/IB2020/056819.

*Primary Examiner* — Eyamindae C Jallow
(74) *Attorney, Agent, or Firm* — Wenderoth, Lind & Ponack, L.L.P.

(57) ABSTRACT

A filling machine (1) includes a dosing station (3) comprising a supporting element (5) and a dosing unit (10) having a dosing cylinder (12) and a piston (13), for filling bodies (101) of capsule (100) with a product (P) picked-up from a tank (4); the supporting element (5) is movable between a lowered picking position (B), in which the dosing unit (10) is inserted in the tank (4) and a dosing position (C) in which the dosing unit (10) faces a body (101); the piston (13) is movable between a first internal position (D) to form a dosing chamber (15) suitable for picking up and retaining a dose (PI) of product (P), a second internal position (E) to reduce a volume of the dosing chamber (15) and compress (Continued)

the dose (PI) and an external position (F) to push the dose (PI) from the dosing cylinder (12) into a body (101).

17 Claims, 7 Drawing Sheets

(51) Int. Cl.
  *A61J 3/07* (2006.01)
  *A61J 3/10* (2006.01)
  *A61K 9/48* (2006.01)
  *B65B 1/26* (2006.01)
  *B65B 63/02* (2006.01)

(56) References Cited

U.S. PATENT DOCUMENTS

| | | | |
|---|---|---|---|
| 9,021,772 | B2 | 5/2015 | Bedetti |
| 11,383,864 | B2 * | 7/2022 | Kim ................. A61J 3/074 |
| 2004/0172925 | A1 | 9/2004 | Ragazzini et al. |
| 2005/0217752 | A1 * | 10/2005 | Facchini ............. A61J 3/074 |
| | | | 141/146 |
| 2006/0064943 | A1 | 3/2006 | Trebbi et al. |
| 2009/0205748 | A1 | 8/2009 | Ansaloni |
| 2009/0229705 | A1 * | 9/2009 | Ansaloni ............. A61J 3/074 |
| | | | 141/238 |
| 2019/0367201 | A1 * | 12/2019 | Jeschke ................ B08B 1/002 |
| 2022/0228903 | A1 * | 7/2022 | Masotti ................ G01G 17/00 |

FOREIGN PATENT DOCUMENTS

| | | | |
|---|---|---|---|
| CN | 102227201 | 10/2011 | |
| DE | 102011015823 | 11/2011 | |
| EP | 2 090 279 | 8/2009 | |
| EP | 2090279 A1 * | 8/2009 | ............. A61J 3/074 |
| EP | 3295920 | 3/2018 | |
| EP | 3369409 | 9/2018 | |
| WO | 01/70171 | 9/2001 | |

* cited by examiner

MACHINE AND METHOD FOR FILLING CAPSULES

The present invention relates to automatic machines for packaging of pharmaceutical and/or food products. In particular, the invention relates to a machine and a method for filling capsules or the like with a pharmaceutical or food or other product.

Various types of filling machines are known, arranged to fill capsules, in particular capsules of the body-cap type made of hard gelatin, with pharmaceutical or food products liquid, in powder, granules, tablets, micro-tablets, delayed-action drugs, etc.

Some known filling machines comprise a transfer turret or wheel, rotating around a vertical axis and provided with housings or seats arranged to receive the capsules, and a plurality of operating stations arranged around the aforementioned transfer turret. During its rotation, the transfer wheel moves the capsules, typically with intermittent motion, through the various operating stations comprising a capsule feeding station, one or more dosing stations and a capsule closing station.

In the feeding station a feeding apparatus is provided which picks up the capsules from a storage and, after having correctly oriented the capsule, inserts the latter ones into the seats of the transfer turret. Suitable means provides for opening the capsules by separating the caps from the bodies.

At the dosing station the product is dispensed in a controlled manner into the body of the capsules.

In the closing station the caps are again coupled to the respective bodies so as to close and recompose the capsules filled with the product which are conveyed out of the filling machine.

In some filling machines the dosing station comprises a dosing turret or wheel, rotatable about a respective vertical axis and typically provided with two groups of volumetric dosing devices, angularly spaced 180° apart from one another with respect to the vertical axis and capable of picking up defined amounts or doses of product from a tank, in a picking position, transferring and then releasing the doses into the capsule bodies, in a releasing position.

The volumetric dosing devices of each group are angularly spaced apart and arranged so as to interact with a corresponding number of capsules housed in the seats of the transfer turret. Each dosing device includes a hollow tube or cylinder, which is arranged parallel to the vertical axis of the dosing turret and is provided with a lower opening, and a respective piston sliding inside the hollow cylinder. The piston forms inside the hollow cylinder a dosing chamber that is inferiorly open so as to receive and retain the product when the cylinder is inserted and plunged into a layer of product contained in a tank. The dosing turret is in fact movable also linearly along the vertical axis between a lowered position and a raised position.

In the lowered position of the dosing turret, while the cylinders of a group of dosing devices are plunged into the product inside the tank, so as to load and pick up respective product doses, the cylinders of the other group of dosing device are superimposed and substantially in contact with respective bodies of capsules to be filled, so as to transfer and release to the capsules the product doses.

When the dosing device is inserted and plunged at a predefined speed into the product layer contained in the tank, the product is inserted and compacted inside the hollow cylinder, in the dosing chamber, forming a sort of "core" of product which constitutes the dose.

The pistons are slidably mounted in the respective cylinders so that they can slide inside and expel the product doses. More precisely, each piston is movable according to an operating stroke between an upper internal position, in which with a lower end portion thereof forms the dosing chamber with the respective hollow cylinder, and a lower external position in which said lower end portion is facing the lower open end of the cylinder so as to empty the dosing chamber and transfer the product to the underlying capsule.

Pushers are mounted on the dosing turret and are arranged to move and push the pistons of dosing devices when the latter ones are positioned above the capsule bodies, along the operating stroke, from the internal position to the external position so as to expel the product doses.

The pushers are generally actuated by one or more pneumatic actuators mounted on the dosing turret. An elastic element, mounted inside the hollow cylinder of the dosing device, returns the piston to the internal position when it is disengaged from the respective pusher.

The upper internal position of the piston can be changed with respect to the hollow cylinder to vary the volume of the dosing chamber. For this purpose, an upper end of the piston that is opposite the lower operating end is provided with a transverse pin which is slidable inside a through slot carried out in the side wall of the cylinder and abutting, in the upper internal position, with an adjustment plate mounted on the dosing turret. The vertical position of the adjustment plate may be varied so as to change the internal upper position of the piston. The transverse pin engaged in the cylinder slot further prevents the piston from escaping from the cylinder, defining the lower external position of the same.

Operating machines are also known in which the dosing turret is rotatable around a vertical axis and the dosing devices and the relative pistons mounted thereon are moved parallel to the vertical axis to load and pick up respective product doses (in the picking position), transfer and then release said doses into the bodies of the capsules (in the releasing position). The movement of the dosing devices and relative pistons is carried out by means of cam mechanisms contained inside the dosing turret.

A drawback of the above-described filling machines is that they are structurally and functionally quite complex and expensive because they require numerous mechanical means (cams) and/or pneumatic means (pneumatic cylinders) to move the dosing turret linearly and/or rotatably, the pistons inside the dosing devices in order to adjust the dosing chamber, the pushers to move the pistons in the dosing devices, or to move the dosing devices with respect to the dosing turret and/or the pistons.

The aforementioned known filling machines also have the drawback of not allowing the accurate dosing of products which are not easily compactable and/or compressible inside the cylinders, for example products in powders, granules, micro-tablets, delayed-action drugs and the like. During the rotation of the transfer turret, especially if carried out at high speed, the product at the lower opening of the hollow cylinder, since it is not sufficiently compacted, tends to detach, thereby causing a variation in the amount of product actually dosed inside the capsule. These dosage variations, especially in the case of pharmaceutical productions, generally are not acceptable.

An object of the present invention is to improve the filling machines and known methods for filling capsules or similar elements with products in powder, granules, tablets, micro-tablets, delayed-action drugs, or the like, in particular pharmaceutical or food products.

Another object is to realize a filling machine and a filling method which allow the reliable, precise and repeatable filling of capsules or similar elements also with products which are difficult to be compacted and/or compressed, such as powders.

A further object is to realize a high-performance filling machine with a simple and robust structure and a reliable and safe operation.

In a first aspect of the invention a filling machine according to claim 1 is provided.

In a second aspect of the invention a method for filling capsules with a product according to claim 10 is provided.

The invention can be better understood and implemented with reference to the attached drawings which illustrate an exemplary and non-limiting embodiment thereof, in which.

Figure 1:
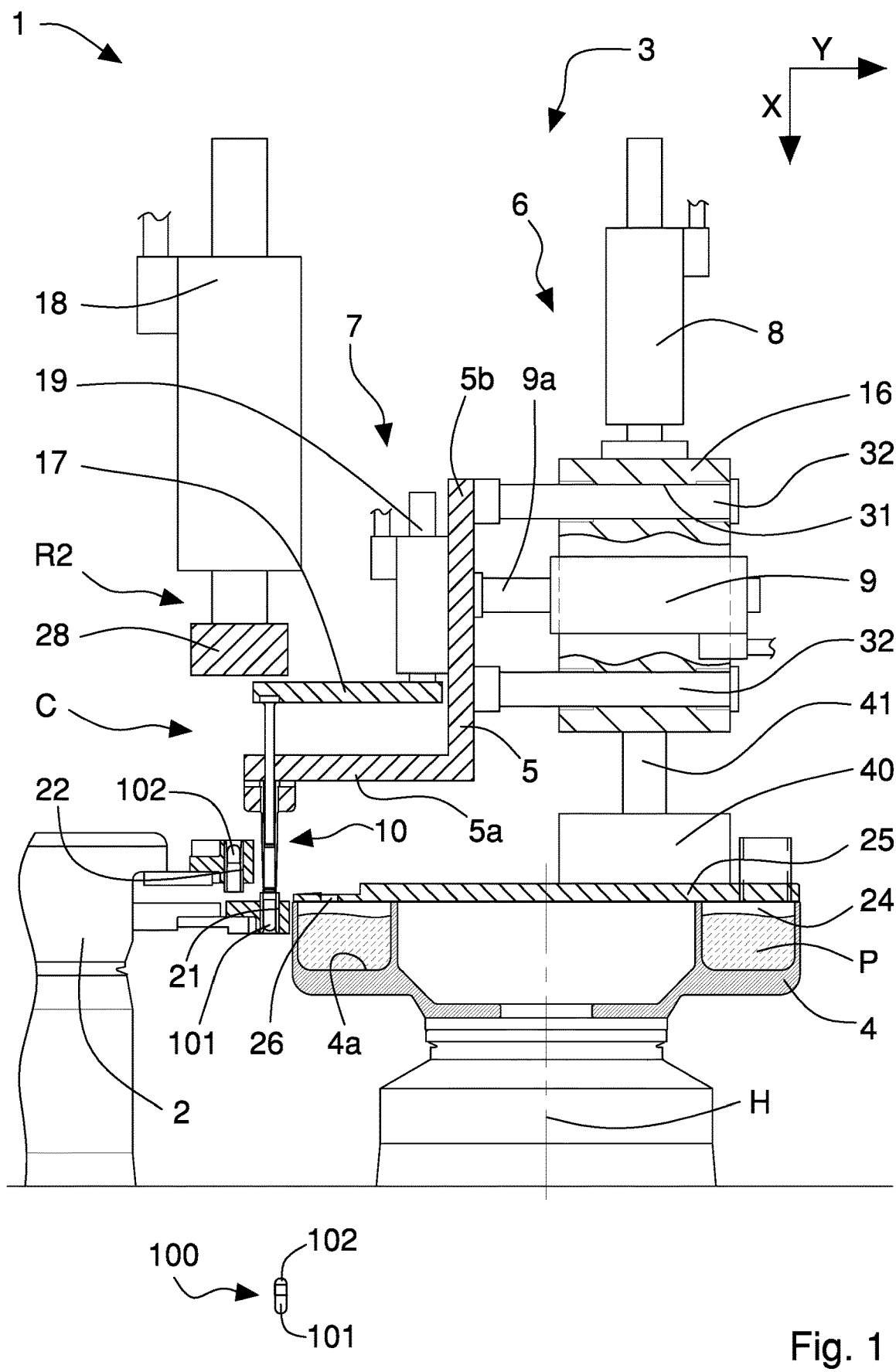
FIG. 1 is an incomplete and partially sectional schematic view of the capsule filling machine according to the invention and a closed capsule to be filled, in particular showing a capsule transfer turret and a dosing station provided with a supporting element of a dosing unit for picking up a dose of product and filling a body of a capsule with the product dose.
Figure 7:
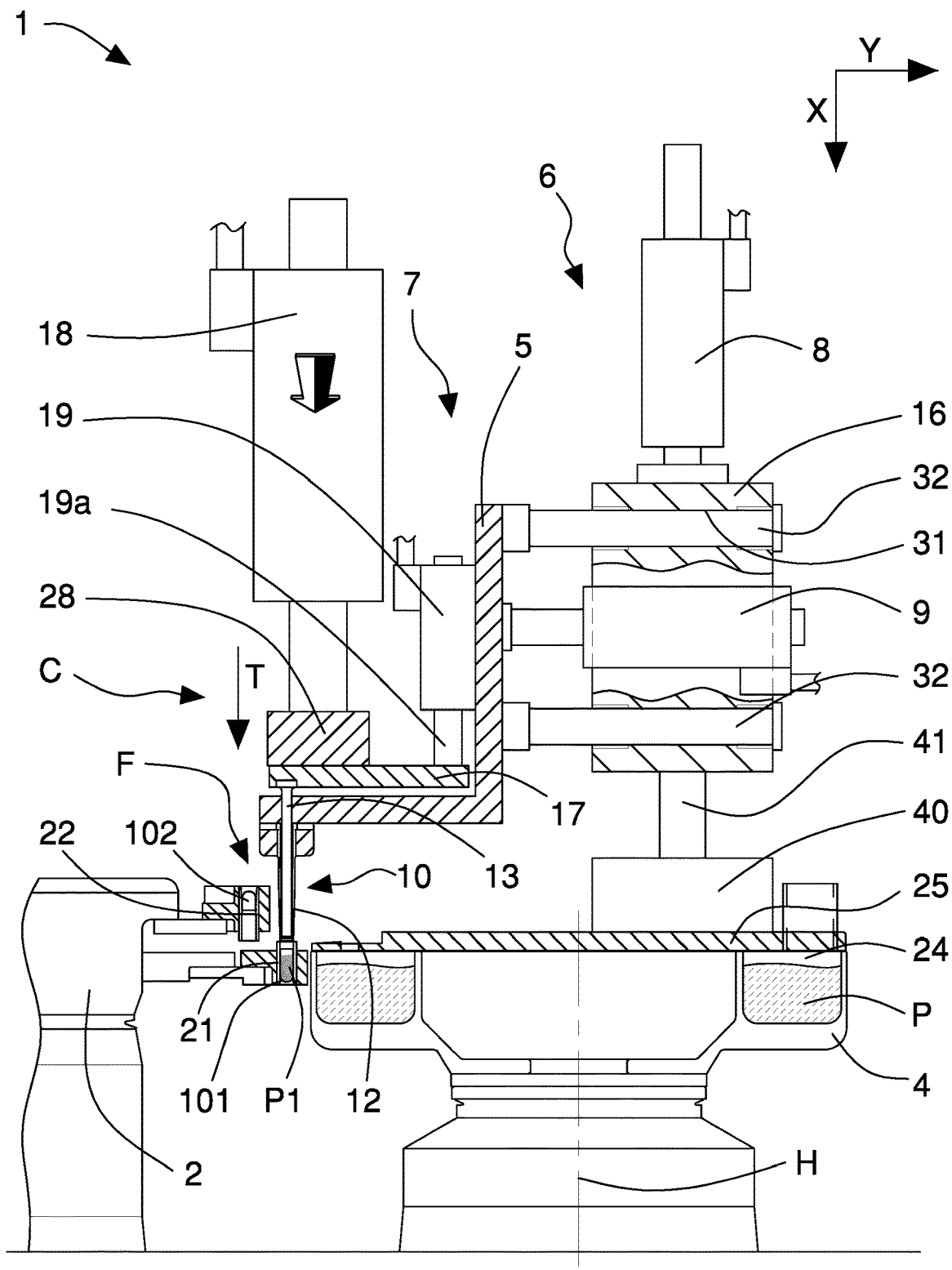
FIG. 7 is a view similar to that of FIG. 1 showing the supporting element in the raised dosing position and the dosing unit with the relative piston in an external position for expelling the product dose in the capsule body.

Referring to FIGS. 1 and 7, the filling machine 1 according to the invention that is arranged to fill capsules 100 or similar containers with a product in powder, granules, tablets, micro-tablets, delayed-action drugs, or the like, in particular a pharmaceutical or food or other product P, comprises a rotating transfer turret 2 and a dosing station 3 of the product P in the capsules 100.

The transfer turret 2 is for example rotatable about a respective axis, in particular vertical, and is arranged to transfer the capsules 100 through successive operating stations of the filling machine 1, known and not illustrated in the figures. The transfer turret 2 is provided with first seats 21 and second seats 22 to respectively house bodies 101 and caps 102 of the capsules 100 (FIG. 1), the latter ones being previously opened in an opening station, of a type known and not illustrated in the figures, which is arranged upstream of the dosing station 3, with reference to a rotation direction of said transfer turret 2.

The dosing station 3 is arranged to fill the bodies 101 of the capsules 100 with a predefined dose P1 of said product P picked up from a tank 4 and comprises a supporting element 5 and at least one dosing unit 10 that is mounted on the supporting element 5 and comprises a hollow and inferiorly open dosing cylinder 12 and a respective piston 13, sliding inside the dosing cylinder 12.

The supporting element 5 is linearly movable by first moving means 6 along two operating directions X, Y, at least between a lowered picking position B, in which the dosing unit 10 is inserted in the tank 4, and a dosing position C, in which the dosing unit 10 is aligned with and facing a body 101 to be filled. The two operating directions comprise a first operating direction X, substantially vertical, and a second operating direction Y almost orthogonal to the first operating direction X and therefore substantially horizontal.

The supporting element 5 is also movable by the first moving means 6 along the first operating direction X from the lowered picking position B to a raised picking position A, in which the dosing unit 10 is disengaged and spaced from the tank 4 to allow the movement of the dosing unit in the position aligned and facing the body 101 to be filled.

The piston 13 of the dosing unit 10 is movable by second moving means 7 inside the dosing cylinder 12 between a first internal position D to form inside the dosing cylinder 12 a dosing chamber 15 suitable for picking up and retaining a dose P1 of product P, in particular when the supporting element 5 is arranged in the lowered picking position B, a second internal position E to reduce a volume of the dosing chamber 15 and compress the dose P1 contained therein while keeping the supporting element 5 in the lowered picking position B, and an external position F to push the dose P1 out of the dosing cylinder 12 and release it into the body 101 when the supporting element 5 is in the dosing position C.

In the lowered picking position B of the supporting element 5, an open end or lower opening 12a of the dosing cylinder 12 almost abuts a bottom wall 4a of the tank 4 so that the piston 13, which is moved from the first internal position D to the second internal position E, can compress the dose P1 of product P against said bottom wall 4a.

The dosing cylinder 12 and the piston 13 of the dosing unit 10 are mounted on the supporting element 5 substantially parallel to the first operating direction X.

The tank 4 includes, for example, a container provided with an annular housing 24 arranged to contain the product P and closed at the top by a lid 25 provided with a hole 26 for the passage of the dosing cylinder 12 of the first dosing unit 10. The tank 4 can rotate about a respective vertical axis H so as to present to the first dosing unit 10 a layer of product P, inside the annular housing 24, having always a constant height and suitable for a correct filling of the dosing cylinder 12.

The first moving means 6 comprises a first electric linear actuator 8 for moving the supporting element 5 along the first operating direction X between the lowered picking position B and the raised picking position A, and a second electric linear actuator 9 for moving the supporting element 5 along the second operating direction Y between the raised picking position A and the dosing position C.

The second moving means 7 comprises a third electric linear actuator 18 for moving the piston 13 of the dosing unit 10 selectively from the first internal position D to the second internal position E or to the external position F according to a first driving direction T, approaching the tank 4 or the body 101, respectively.

The second moving means 7 further comprises a fourth electric linear actuator 19 for moving the piston 13 from the second internal position E or from the external position F to the first internal position D according to a second driving direction V, away from the tank 4 or the body 101, respectively.

The fourth electric linear actuator 19 further allows to vary the first internal position D of the piston 13 with respect to the lower opening 12a of the dosing cylinder 12 so as to modify the volume of the dosing chamber 15 and thus the volume/amount of the dose P1 of product P to be dosed.

The electric linear actuators 8, 9, 18, 19 comprise respective electric linear motors, for example of the type with a magnetic slider that slides inside a linear stator, or respective actuators provided with a rotary electric motor coupled to a lead screw transmission system, possibly by interposition of a motion reducer.

The first moving means 6 also comprises a first moving element 16 that is slidably supported by a supporting frame 40 of the filling machine 1, is movable along the first operating direction X by the first electric linear actuator 8 and is arranged to slidably support the supporting element 5, which is thus movable along the second operating direction Y, driven by the second electric linear actuator 9. More precisely, the first moving element 16 is slidably mounted on a supporting upright 41 fixed to the supporting frame 40 and has one or more seats 31 adapted to slidably receive respective sliding pins 32 of the supporting element 5. The latter has, for example, a substantially "L" shape and includes a first portion 5a parallel to the second operating direction Y, i.e., almost horizontal, to which the dosing unit 10 and more precisely the dosing cylinder 12 thereof is fixed, and a second portion 5b parallel to the first operating direction X to which the sliding pins 32 are fixed, extending in the opposite direction to the direction of the first portion 5a along the second operating direction Y.

The first electric linear actuator 8, which is fixed to the supporting frame 40 of the filling machine 1 by means of connection means of known type and not illustrated, acts on the first moving element 16 by means of a respective stem 8a.

The second electric linear actuator 9 is fixed to the first moving element 16 and acts on the supporting element 5 by means of a respective stem 9a.

The second moving means 7 comprises a second moving element 17 connected to, and acting on, the piston 13 and movable relative to the supporting element 5 along the first operating direction X selectively by means of the third electric linear actuator 18 or the fourth electric linear actuator 19.

More precisely, the second moving element 17 is actuated by the third electric linear actuator 18 in order to move the piston 13 of the dosing unit 10 from the first internal position D to the second internal position E or to the external position F according to the first driving direction T, while it is actuated by the fourth electric linear actuator 19 according to the opposite second driving direction V, to move the piston 13 from the second internal position E or from the external position F to the first internal position D.

The second moving element 17 is connected to a second end 13a of the piston 13 opposite a first end 13b of the piston 13 contained inside the dosing cylinder 12.

A beating element 28, or ram, is provided that is connected to, and moved by, the third electric linear actuator 18, in particular is fixed to a stem 18a thereof, so as to hit with a definite impulsive force the second moving element 17 and then move the piston 13 to the second internal position E or to the external position F at high speed and exerting a high pushing/compressive force on the dose P1 contained in the dosing chamber 15, respectively to compress the product contained in the dosing chamber 15 during the picking step or to expel the dose P1 from the dosing unit 10 and insert the dose in the body 101.

The third electric linear actuator 18 may be adjusted so as to hit the second moving element 17 with different impulsive forces, in particular with a first higher impulsive force to move the piston 13 to the second internal position E in the powder compression step and a second lower impulsive force to move the piston 13 to the external position F in the dose P1 expulsion step.

In the lowered picking position B of the supporting element 5, the beating element 28 is actuated by the third electric linear actuator 18 from a first rearward position R1, in which the beating element is spaced from the second moving element 17 by a definite distance, to a first working position in which the bearing element pushes the piston 13 to the second internal position E.

In the dosing position C of the supporting element 5, the beating element 28 is moved with impulsive motion by the third electric linear actuator 18 from a second rearward position R2, in which beating element is spaced from the second moving element 17 by a definite distance, to a second working position in which beating element pushes the piston 13 to the external position F.

In the illustrated embodiment, the second moving element 17 is directly supported by the fourth electric linear actuator 19 which is fixed to the supporting element 5. In particular, a body of the fourth electric linear actuator 19 is fixed to the second portion 5b of the supporting element 5, and a end of a movable stem 19a of said fourth electric linear actuator 19 is fixed and supports the second moving element 17.

As better explained in the following description, the fourth electric linear actuator 19 is selectively activated to move the second moving element 17 according to the second driving direction V or deactivated to enable the second moving element 17 to slide freely and in particular to be moved by the third electric linear actuator 18 according to the first driving direction T, in particular to be hit and moved by the beating element 28.

The dosing station 3 further comprises air suction means, of known type and not illustrated in the figures, connected to the dosing unit 10 through a respective conduit 36 in order to suck air from inside the respective dosing cylinder 12 and cooperate in picking up the dose P1 during the picking of the product P from the tank 4 and retaining the dose inside the dosing chamber 15, in particular during the movement of the supporting element 5 along the two operating directions X, Y.

It is provided that in the filling machine 1 of the invention the dosing station 3 includes a plurality of dosing units 10 supported by the supporting element 5 and arranged parallel to one another and regularly spaced, linearly or along an arc of circumference so as to form a group of dosing units 10.

In this case, the second moving means 7 act on the respective pistons 13 of said plurality of dosing units 10, and in particular the second moving element 17 is connected to said pistons 13.

The number of dosing units 10 is equal to the number of bodies 101, housed in the first seats 21 of the transfer turret 2 to be filled in a single operation or step. The pitch or angular distance between two adjacent dosing units 10 is equal to the pitch or distance between two adjacent first seats 21 of the transfer turret 2.

In a variant of the filling machine 1 of the invention that is not shown in the figures, mechanical (blades) or pneumatic (air blows) scraping means are arranged to scrape the lower opening 12a of the dosing cylinder 12 and detach the excess of product P from the dose P1, when the dosing unit 10 is extracted and raised from the tank 4, in the raised dosing position A of the supporting element 5, with the piston 13 arranged in the second internal position E. After scraping, the piston 13 is moved to the first internal position D so as to bring the dose P1 of compressed and compacted product completely inside the dosing cylinder 12.

The operation of the filling machine 1 of the invention and in particular of the dosing station 3 comprises in a first step (FIG. 2) to arrange the supporting element 5 in the raised picking position A in which the first dosing unit 10 is arranged above the tank 4 of the product P, and in particular is aligned with the hole 26 of the lid 25 of the tank 4.

Preliminarily, the fourth electric linear actuator 19 is actuated so as to move the second moving element 17 and adjust the first internal position D of the piston 13 of the dosing unit 10 with respect to the lower opening 12a of the corresponding dosing cylinder 12, so as to form within the latter a dosing chamber 15 having a predetermined volume.

Figure 3:
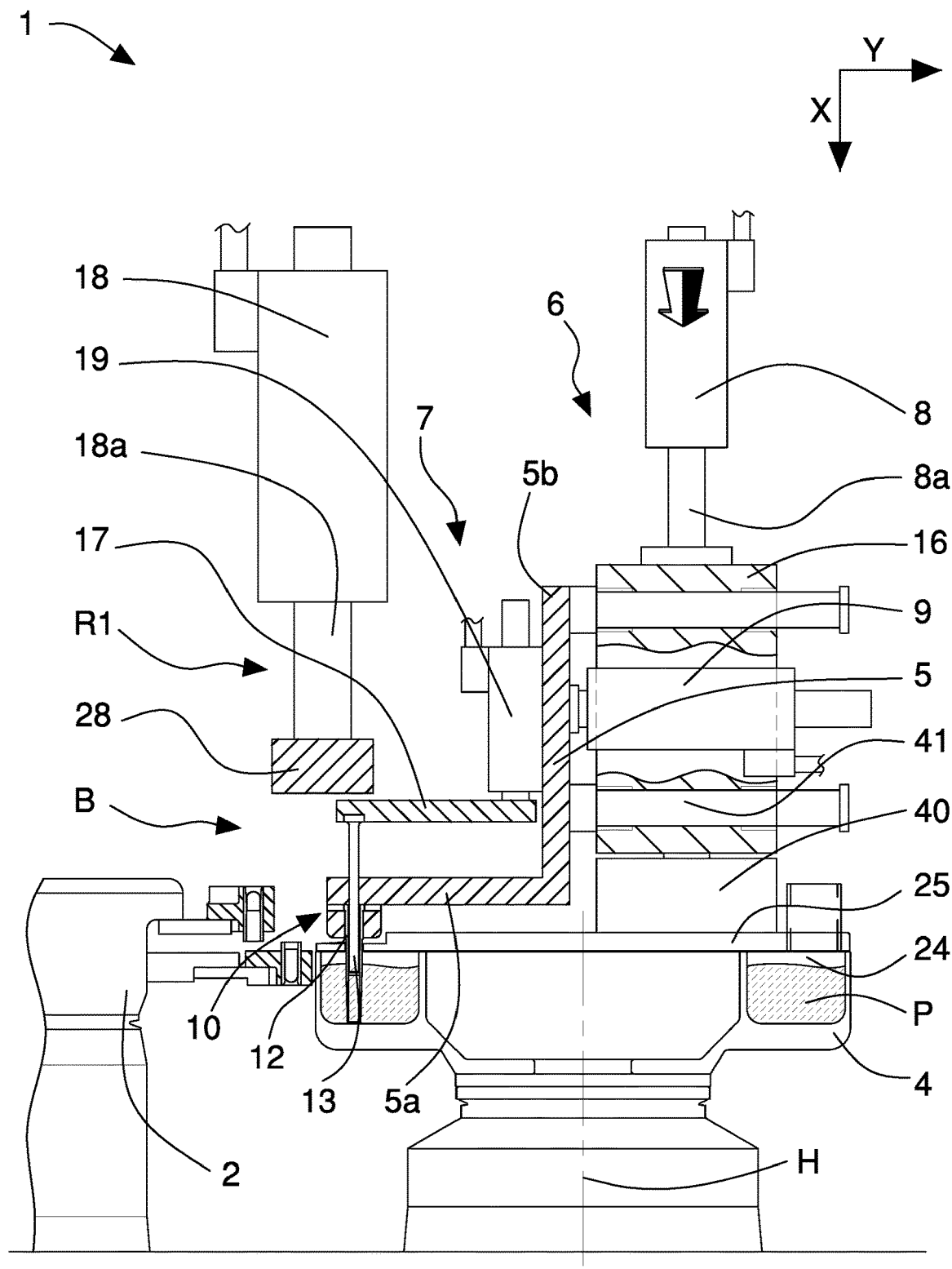
FIG. 3 is a view similar to that of FIG. 1 showing the supporting element of the dosing unit in a lowered picking position B in which the dosing unit is inserted in a tank to pick up a product dose.
Figure 3A:
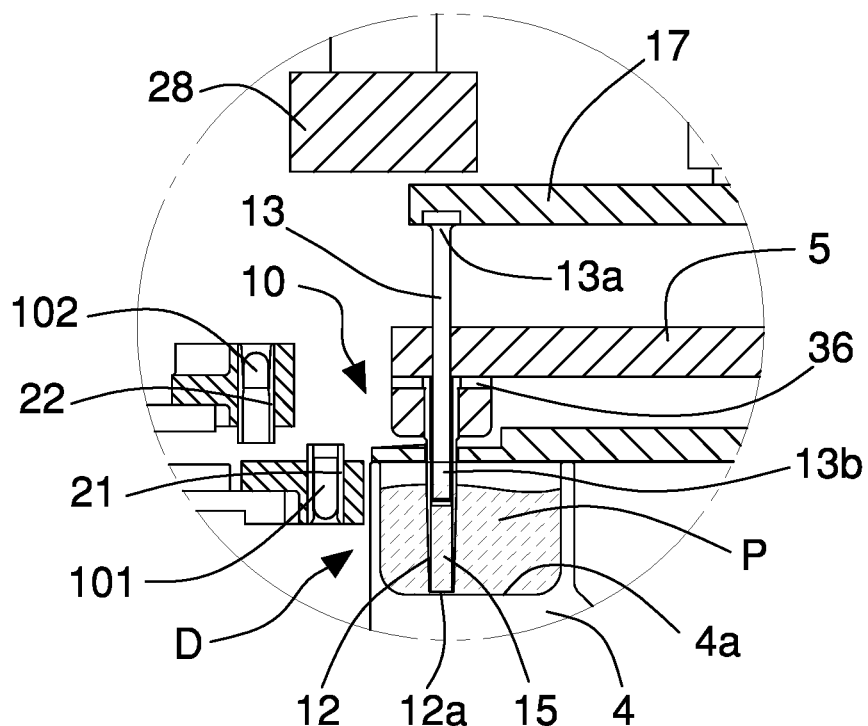
FIG. 3A is an enlarged detail of FIG. 3 showing in particular the dosing unit with the relative piston in the first internal position.

In a second step (FIGS. 3 and 3A) the supporting element 5 is linearly moved along the first operating direction X from the raised picking position A to the lowered picking position B by the first electric linear actuator 8 of the first moving means 6 so that the dosing unit 10 is inserted or "plunged" inside the tank 4, passing through the hole 26 of the lid 25, in the layer of product P contained in the annular housing 24. As known, by inserting the dosing cylinder 12 in the layer of product P a portion of the latter penetrates inside the dosing chamber 15, forming a "core" or dose P1 of product.

The dose P1 of product picked up from the tank 4, can also be introduced and retained in the dosing chamber 15 also by virtue of the air suction performed inside the dosing cylinder 12 by the air suction means connected to the dosing unit 10 through a respective conduit 36.

Figure 4:
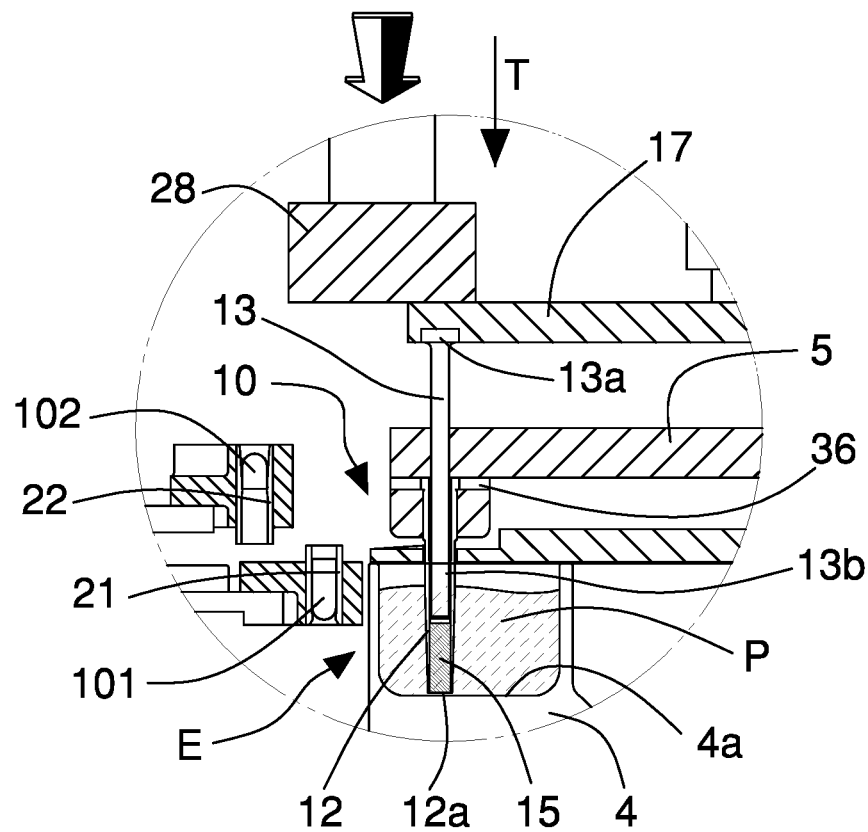
FIG. 4 is a detail similar to that of FIG. 3A showing the dosing unit with the piston in a second internal position for compressing the product dose.

In a third step (FIG. 4), the third electric linear actuator 18 of second moving means 7 is actuated so that the beating element 28 hits with a definite impulsive force the second moving element 17 and then the piston 13 until the latter is positioned in the second internal position E. In this way the piston 13 is moved according to the first driving direction T with an impulsive motion with high speed and such as to exert a high thrust/compression force on the dose P1 contained in the dosing chamber 15 so as to compress the product of the dose P1, in particular against the bottom wall 5a of the tank 4.

The compression allows compacting optimally the product, especially a powder product, with air leaking through a cylindrical meatus formed by the piston 13 and an internal wall of the dosing cylinder 12. In addition, the dose P1 strongly adheres to the internal walls of the dosing cylinder 12, making more difficult to detach the product in the subsequent operating steps.

While driving of the third electric linear actuator 18, the fourth electric linear actuator 19 is deactivated or made "idle" to allow the second moving element 17 to slide freely and then be moved with impulsive motion by the third electric linear actuator 18 according to the first driving direction T.

Said third step of compression may not be performed if it is not necessary to compress/press the product in the dosing chamber.

In a fourth step, the third electric linear actuator 18 is actuated so as to disengage and move the beating element 28 away from the second moving element 17 so as to allow the activated third electric linear actuator 18 to return the piston 13 to the first internal position D, thereby increasing a volume of the dosing chamber 15, and move the product dose P1 further inside the dosing cylinder 12.

The retracting movement of the piston 13 inside the dosing cylinder 12 substantially produces a "suction and dragging effect" of the product dose P1 inside the dosing chamber 15, allowing a peripheral portion of the dose to be moved away from the lower opening 12a of the dosing cylinder 12. In this way, during the movement of the supporting element 5 in order to position the dosing unit 10 at the body 101 to be filled, said peripheral portion of the dose P1, since it is completely contained inside the dosing cylinder 12 and adheres to the internal walls of thereof, is more difficult to detach and fall from the dosing cylinder 12 due to air flows and/or vibrations generated by the translation of the dosing element 5.

Figure 5:
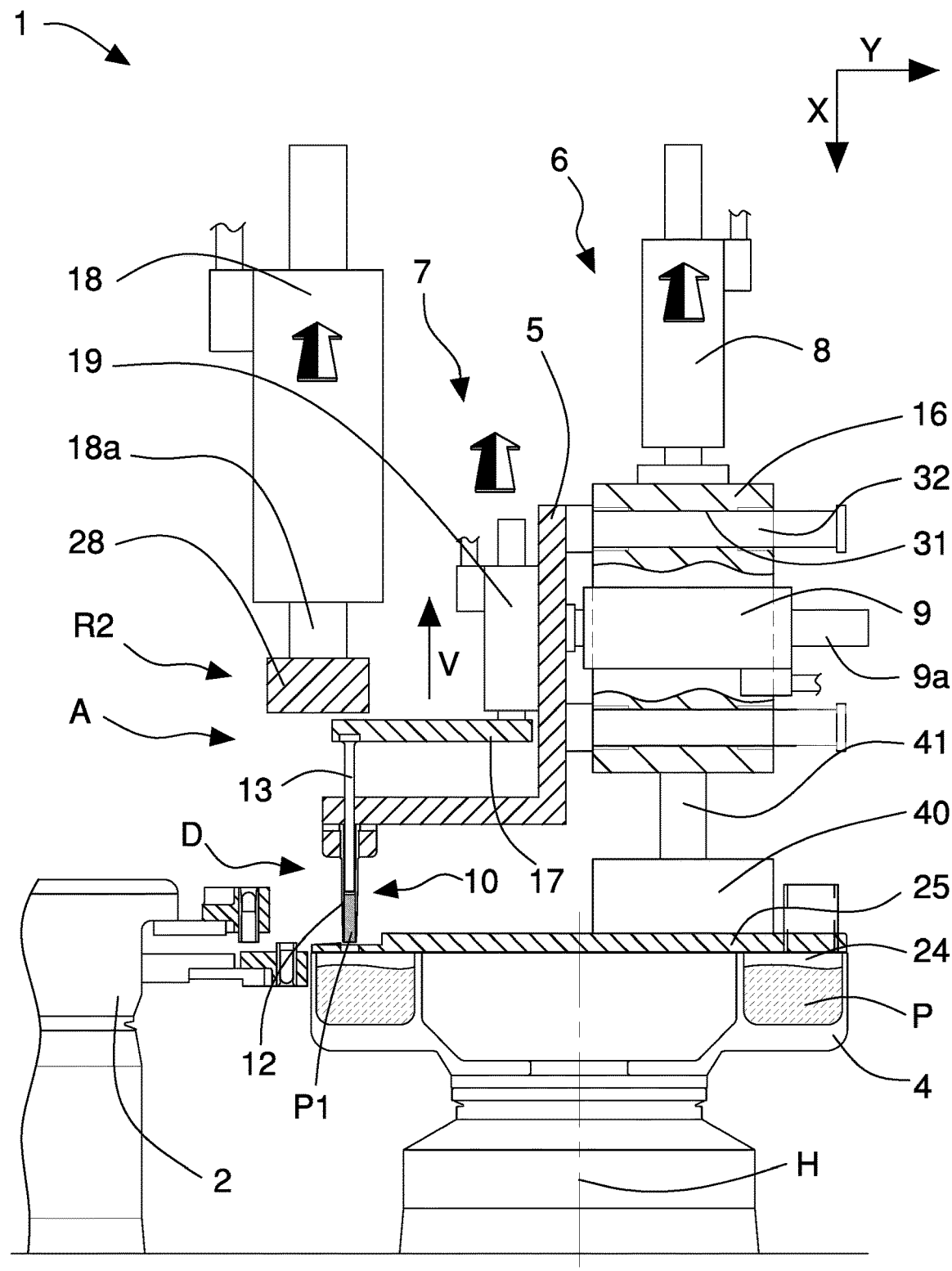
FIG. 5 is a view similar to that of FIG. 1 showing the supporting element in the raised picking position and the dosing unit provided with a product dose with the piston in the first internal position.

In a fifth step (FIG. 5), the supporting element 5 is moved by the first electric linear actuator 8 from the lowered picking position B to the raised picking position A so as to disengage the dosing unit 10 from the product P and the tank 4 and allow the subsequent movement of the dosing unit.

It is also possible that the fourth step and the fifth step coincide, i.e. that simultaneously with the raising movement of the supporting element 5, the piston 13 of the dosing unit 10 is moved by the first electric linear actuator 8 in the first internal position D, so as to increase the volume of the dosing chamber 15 and move the dose P1 of product picked up from the tank 4 further inside the dosing cylinder 12.

Figure 6:
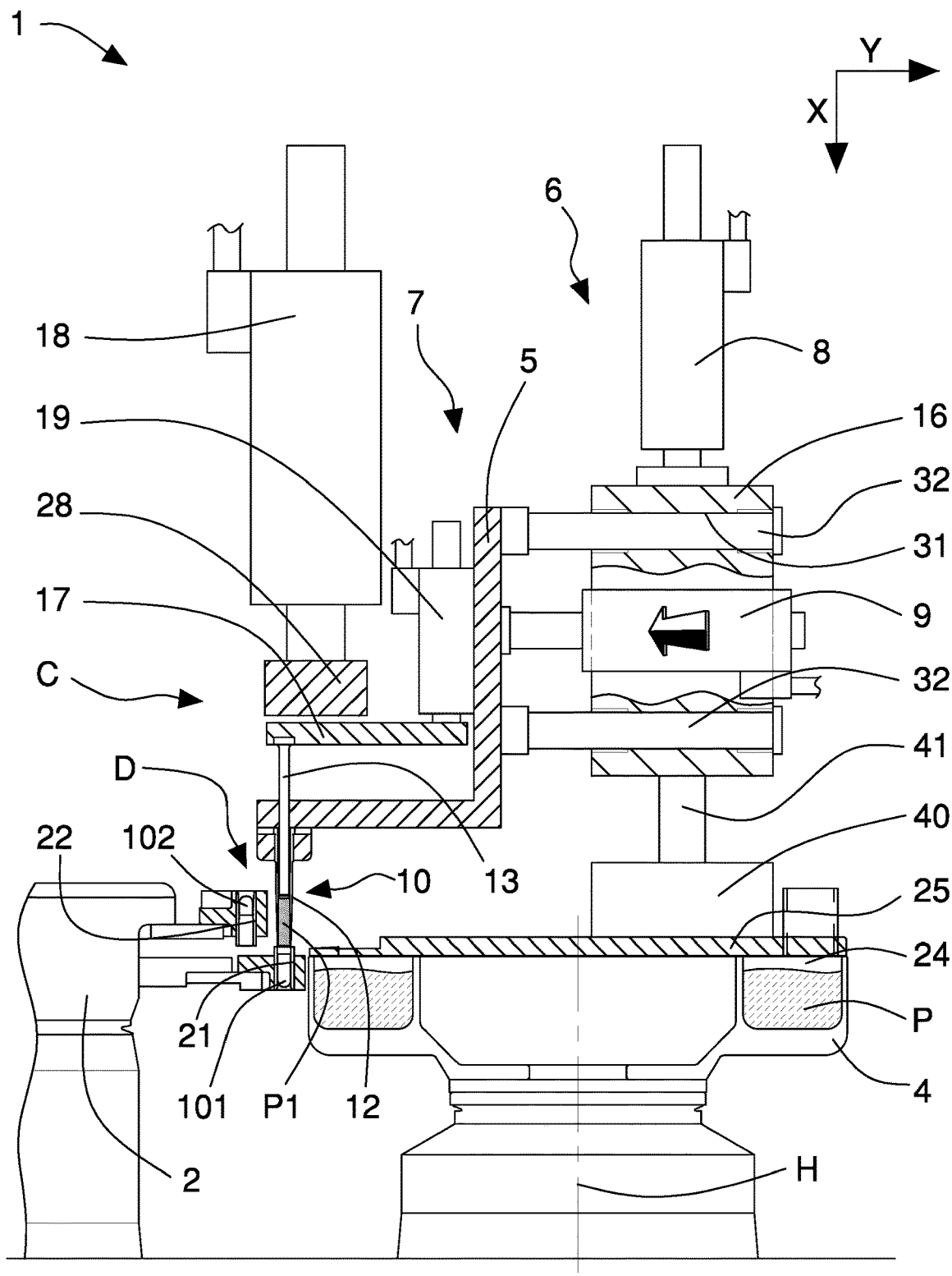
FIG. 6 is a view similar to that of FIG. 1 showing the supporting element in a dosing position and the dosing unit provided with a product dose superimposed and aligned with a body of a capsule to be filled and with the piston in the first internal position.

In a sixth step (FIG. 6) the supporting element 5 is moved along the second operating direction Y by the second electric linear actuator 9 of the first moving means 6 in the dosing position C in which the first dosing unit 10 is aligned and facing a first seat 21 of the transfer turret 2, in particular with the lower opening 12a of the dosing cylinder 12.

In a seventh step (FIG. 7) the third electric linear actuator 18 is actuated so that the beating element 28 hits with a definite impulsive force the second moving element 17 and then the piston 13 until the latter is arranged in the external position F so as to expel the dose P1 from the dosing cylinder 12 and release it into the body 101. The impulsive force exerted by the third electric linear actuator 18 by means of the beating element 28 on the second moving element 17 may be different, in particular lower, than the impulsive force exerted in the third compression step.

Also in this step, while driving the third electric linear actuator 18, the fourth electric linear actuator 19 is deactivated or made "idle" to allow the second moving element 17 to slide freely and then be moved with impulsive motion by the third electric linear actuator 18 according to the first driving direction T.

Any air suction inside the dosing cylinder 12 is deactivated in this seventh step so as not to hinder the expulsion of the dose P1.

In an eighth step (FIG. 1), the third electric linear actuator 18 is actuated so as to disengage and move the beating element 28 away from the second moving element 17 so as to allow the fourth electric linear actuator 19, which is actuated, to return the piston 13 to the first internal position D to form the dosing chamber 15.

Figure 2:
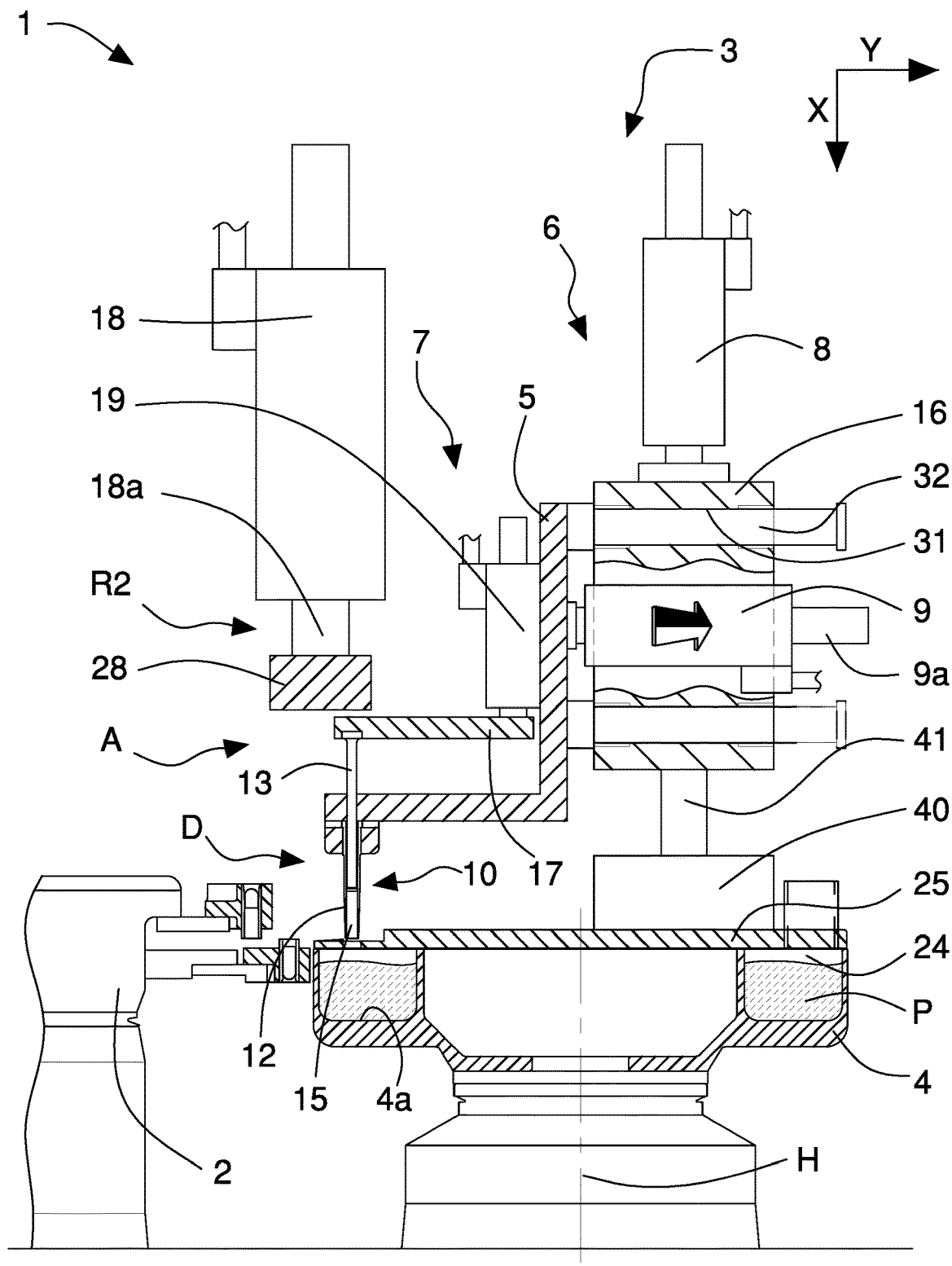
FIG. 2 is a view similar to that of FIG. 1 illustrating the supporting element of the dosing unit in a raised picking position A and the dosing unit with a relative piston in a first internal position.

In a ninth step or during the eighth step, the supporting element 5 is moved by the second electric linear actuator 9 from the dosing position C to the raised picking position A in order to arrange the dosing unit 10 above and aligned with the hole 26 of the lid 25 of the tank 4 (FIG. 2).

Once the body 101 of a capsule 100 has been filled with the dose P1 of product P, the transfer turret 2 is rotated at a definite angle or pitch so as to place a subsequent body 101 to be filled and steps 1 to 9 are repeated in the dosing station 3.

It should be noted that the description of the operation of the filling machine 1 is the same also in the case of a plurality of dosing units 10, arranged to simultaneously fill a plurality of bodies 101 (in equal number to that of the dosing units 10) with respective doses P1 of product so as to increase a productivity of the filling machine 1 of the invention.

The method according to the invention for filling capsules 100 or similar containers with a product P in powder, granules, tablets, micro-tablets, delayed-action drugs, or the like comprises the following steps:

picking up a dose P1 of product P from a tank 4 by means of at least one dosing unit 10 mounted on a supporting element 5, the dosing unit 10 comprising a respective hollow and inferiorly open dosing cylinder 12 and a respective piston 13 movable inside the dosing cylinder 12 and arranged in a first internal position D to form a dosing chamber 15 inside the dosing cylinder 12 suitable for receiving and retaining the dose P1 of product P;

moving the piston 13 from the first internal position D to a second internal position E so as to reduce a volume of the dosing chamber 15 and compress said dose P1, in particular against a bottom wall 4a of the tank 4;

moving the dosing unit 10 at a body 101 of a capsule 100 in order to push the dose P1 of product P out of the dosing cylinder 12 and release the dose into the body 101 by moving the piston 13 inside the dosing cylinder 12 to an external position F;

in which the step of moving the dosing unit 10 is carried out by activating first moving means 6 for moving the supporting element 5 along two operating directions X,Y, at least between a lowered picking position B, in which the dosing unit 10 is inserted in the tank 4, and a dosing position C, in which the same dosing unit 10 is aligned and facing the body 101.

It is possible to move the piston 13 from the first internal position D to the second internal position E by imparting to the piston 13 a definite impulsive force so as to move the piston at high speed and with a high pushing force acting on the dose P1 contained in the dosing chamber 15 for an optimal compression of the product.

The method further provides, before moving the dosing unit 10 and after moving the piston 13 to the second internal position E, to move the piston 13 to the first internal position D in order to increase a volume of said dosing chamber 15 and further move inside the dosing cylinder 12 the dose P1 of product P, in particular powder product, picked up from the tank 4 and compressed, in order to prevent detachments of product P from the dose P1 during movement of the dosing unit 10.

Picking up the dose P1 of product comprises inserting or "plunging" the dosing unit 10 into a layer of product P contained in the tank 4 so that an open end or lower opening 12a of the dosing cylinder 12 substantially abuts the bottom wall 4a of said tank 4 and a part of the product P penetrates inside the dosing chamber 15 formed by the piston 13 in the hollow dosing cylinder 12, thereby obtaining the product dose P1.

Moving the supporting element 5 to move the dosing unit 10 comprises linearly moving the supporting element 5 on which the dosing unit 10 is mounted along a first operating direction X between the lowered picking position B and a raised picking position A, in which the dosing unit 10 is disengaged and spaced from the tank 4, and along a second operating direction Y orthogonal to the first operating direction X between the raised picking position A and the dosing position C, in particular by means of a first electric linear actuator 8 and a second electric linear actuator 9.

The method also comprises moving the piston 13 of the dosing unit 10 from the first internal position D to the second internal position E or to the external position F, in particular according to a first driving direction T approaching the tank 4 or the body 101, by means of a third electric linear actuator 18.

The method comprises moving the piston 13 of the dosing unit 10 from the second internal position E or from the external position F to the first internal position D, in particular according to an opposite second driving direction V away from the tank 4 or the body 101, by means of a fourth electric linear actuator 19.

The method then comprises moving the piston 13 of the dosing unit 10 during the compression of the dose P1 of product P in the tank 4 (second internal position E) and during the expulsion thereof into the body 101 of the capsule 100 (external position F) with a very high speed and pushing force that are greater than those necessary to return the piston 13 to the first internal position D.

It is also provided to vary the first internal position D of the piston 13 in the respective dosing cylinder 12 by means of the fourth electric linear actuator 19 so as to modify a volume of the dosing chamber 15 and then a volume of the dose P1 of product P picked up from the dosing unit 10.

It is also provided to vary the second internal position E of the piston 13 in the respective dosing cylinder 12 by means of the third electric linear actuator 18 so as to modify the volume of the dosing chamber 15 and therefore the compression rate of the product P contained therein, in particular according to physical/chemical characteristics of the product. The method also comprises sucking air inside the dosing cylinder 12 of the dosing unit 10 to help to pick up the dose P1 of product P from the tank 4 and to retain the dose P1 inside the dosing chamber 15 during the movement of the dosing unit 10, in particular during a vertical raising movement of the supporting element 5 along the first operating direction X from the lowered picking position B to the raised picking position A, and during a horizontal movement of the supporting element 5 along the second operating direction Y from the lowered picking position B to the dosing position C.

In a variant of the method for filling of the invention it is further provided, after picking up the dose P1 of product P and before moving the piston 13 from the second internal position E to the first internal position D, to scrap the lower opening 12a of the dosing cylinder 12 of the dosing unit 10 to detach an excess of product P from the dose P1.

The filling machine 1 and the method of the invention thus allow to fill capsules or similar elements in a reliable, accurate and repeatable way also with products which are difficult to compact and/or compress, such as for example powders, granules, tablets, micro-tablets, delayed-action drugs, i.e. products more susceptible to outflow from the dosing unit during the movement thereof from the tank 4 of product P for forming the dose P1, to the first seat 21 of the transfer turret 2 for filling the body 101 of the capsule 100. In particular, thanks to the compression performed by the piston 13 during the step of picking the dose P1, a powder product contained in the dosing chamber 15 can be effectively compressed and compacted. In fact, the compressing and compacting movement is performed by the beating element 28 which is actuated by the third electric linear actuator 18, of adequate power, so as to hit with a specific and selectable impulsive force the second moving element 17 and then move the piston 13 at high speed in the second internal position E so as to exert a high thrust or compression force on the dose P1, capable of releasing the air contained in the product (typically powder).

The third electric linear actuator 18 can be easily adjusted to calibrate the speed, push/compression force, and stroke of the piston 13 based on the specific product P to be compressed.

Likewise, the third electric linear actuator 18 can be suitably adjusted so that the beating element 28 hits with a definite impulsive force the second moving element 17 and then the piston 13 in the step of expelling the dose P1 from the dosing cylinder 12 into the body 101. The impulsive force exerted by the third electric linear actuator 18 by means of the beating element 28 on the second moving element 17 may be lower than the impulsive force exerted in the third step of compression.

The rising movement of the piston 13 in the second driving direction V is instead performed by the fourth electric linear actuator 19 which can have much smaller dimensions and power, having to move only the piston 13. The fourth electric linear actuator 19 allows controlling in a precise, accurate and repeatable way the motion of the piston 13, in particular allows to select one of a plurality of first internal positions D which define respective volumes of the dosing chamber 15 of the dosing unit 10.

As previously emphasized, the rearward movement of the piston 13 inside the dosing cylinder 12 after the compression of the powder in the dosing chamber 15 causes a dragging by "suction" of the dose P1 of product inside the dosing chamber 15, which allows to move the peripheral portion of the dose P1 away from the lower opening 12*a* of the dosing cylinder 12. In this way, during the movement of the supporting element 5 (to align the dosing unit 10 to a first seat 21 of the transfer turret 2), said peripheral portion of dose P1 is completely contained inside the dosing cylinder 12 and, adhering to the internal walls thereof thanks to the compression previously performed, it is more difficult to detach due to air flows and/or vibrations generated by the movement of the supporting element 5.

This solution together with the compression of the dose P1 at the picking step is particularly advantageous in the case of products P in powder form which are more difficult to compress inside the dosing cylinder 12 and therefore more susceptible to outflow during the movement of the dosing unit 10, in particular during the translation movement of the supporting element 5.

The latter is moved linearly along the first operating direction X between the raised picking position A and the lowered picking position B and vice versa by the first electric linear actuator 8, while it is moved along the second operating direction Y, from the tank 4 to the transfer turret 2, i.e. from the raised picking position A to the dosing position C and vice versa, by the second electric linear actuator 9.

Thanks to the use of electric linear actuators 8, 9, 18, 19 for moving the supporting element 5 (which supports the dosing units 10) and the pistons 13 of the dosing units 10, the filling machine 1 of the invention, besides having high performance, has a particularly simple, economical and robust structure and a reliable and safe operation.

The invention claimed is:

1. A filling machine for filling capsules or similar containers with a product in powder, granules, tablets, microtablets, delayed-action drugs or similar, comprising a rotating transfer turret, arranged to transfer said capsules through successive operating stations and provided with at least seats to house bodies and caps of said capsules, and at least one dosing station that is arranged to fill said bodies with a product picked-up from a tank and comprising a supporting element and at least one dosing unit mounted on said supporting element and comprising a hollow and inferiorly open dosing cylinder and a respective piston, said supporting element being movable by a first moving system along two operating directions at least between a lowered picking position, in which said dosing unit is inserted in said tank, and a dosing position, in which said dosing unit is aligned with and facing a body of a capsule, said respective piston of said dosing unit being movable by a second moving system inside said dosing cylinder between a first internal position to form inside said dosing cylinder a dosing chamber suitable for picking up and retaining a dose of product, a second internal position to reduce a volume of said dosing chamber and compress said product dose in said dosing chamber in said lowered picking position of said supporting element, and an external position to push said dose out of said dosing cylinder and release the dose into a body in said dosing position of said supporting element.

2. The filling machine according to claim 1, wherein said first moving system comprises a first electric linear actuator for moving said supporting element along said first operating direction between said lowered picking position and a raised picking position, in which said dosing unit is disengaged and spaced from said tank, and a second electric linear actuator for moving said supporting element along a second operating direction substantially orthogonal to said first operating direction between said raised picking position and said dosing position.

3. The filling machine according to claim 2, wherein said first moving system comprises a first moving element slidably supported by a supporting frame of said filling machine and movable along said first operating direction by said first electric linear actuator, said first movement element slidably supporting said supporting element that is movable along said second operating direction by said second electric linear actuator.

4. The filling machine according to claim 1, wherein said second moving system comprises a third electric linear actuator for moving said piston of said at least one dosing unit from said first internal position to said second internal position or to said external position according to a first driving direction approaching said tank or said body respectively, and a fourth electric linear actuator for moving said piston from said second internal position or from said external position to said first internal position according to a second driving direction moving away from said tank or said body respectively.

5. The filling machine according to claim 4, wherein said second moving system comprises a second moving element connected to, and acting on, said piston and movable with respect to said supporting element along said first operating direction selectively by said third electric linear actuator or by said fourth electric linear actuator.

6. The filling machine according to claim 5, wherein said second moving element is supported by said fourth electric linear actuator, which is fixed to said supporting element, and is coupled to a second end of said piston that is opposite to a first end thereof enclosed in said dosing cylinder.

7. The filling machine according to claim 4, wherein said fourth electric linear actuator can be selectively activated to move said second moving element according to said second driving direction or deactivated to enable said second moving element to slide freely and be moved by said third electric linear actuator according to said first driving direction.

8. The filling machine according to claim 1, wherein in said lowered picking position of said supporting element an open end of said dosing cylinder substantially abuts a bottom wall of said tank so that said piston when moved from the first internal position to the second internal position compresses said dose of product against said bottom wall.

9. The filling machine according to claim 1, wherein said dosing station includes a plurality of dosing units supported by said supporting element and arranged spaced apart from one another, said second moving system acting on respective pistons of said plurality of dosing units.

10. The filling machine according to claim 3, wherein by said second electric linear actuator is fixed to said first moving element.

11. A method for filling capsules or similar containers with a product in powder, granules, tablets, micro-tablets, delayed-action drugs or similar, comprising:
  picking-up a dose of product from a tank by means of a dosing unit mounted on a supporting element, said dosing unit comprising a respective hollow and inferiorly open dosing cylinder and a respective piston movable inside the dosing cylinder and arranged in a first internal position to form a dosing chamber suitable for receiving and retaining said dose of product;
  moving said piston from said first internal position to a second internal position so as to reduce a volume of said dosing chamber and compress said dose against a bottom wall of said tank;
  moving said dosing unit at a body of a capsule in order to push said dose of product out of said dosing cylinder and release the dose into said body by moving said piston inside said dosing cylinder in an external position;
  wherein said moving said dosing unit is carried out by activating a first moving system for moving said supporting element along two operating directions at least between a lowered picking position, in which said dosing unit is inserted in said tank, and a dosing position, in which said dosing unit is aligned with and facing said body.

12. The method according to claim 11, comprising before said moving said dosing unit and after moving said piston in said second internal position, moving said piston in said first inner position so as to increase a volume of said dosing chamber and moving more inside said dosing cylinder said dose of product picked-up in said tank and compressed in order to prevent detachments of product from said dose during moving said dosing unit.

13. The method according to claim 11, wherein said moving said supporting element for moving said dosing unit comprises moving said supporting element along a first operating direction between said lowered picking position and a raised picking position, in which said dosing unit is disengaged and spaced from said tank, and along a second operating direction, orthogonal to said first operating direction, between said raised picking position and said dosing position.

14. The method according to claim 11, comprising moving said piston of said dosing unit from said first internal position to said second internal position or to said external position according to a first driving direction approaching said tank or said body by means of a third electric linear actuator.

15. The method according to claim 11, comprising moving said piston of said dosing unit from said second internal position or from said external position to said first internal position according to a second driving direction moving away from said tank or from said body by means of a fourth electric linear actuator.

16. The method according to claim 11, comprising varying said first internal position of said piston in said respective dosing cylinder by means of a fourth electric linear actuator so as to modify a volume of said dosing chamber and therefore of said dose of product picked-up by said dosing unit.

17. The method according to claim 13, comprising moving said supporting element along said first operating direction and along said second operating direction by means of a first electric linear actuator and a second electric linear actuator.

* * * * *